United States Patent [19]
Adams et al.

[11] Patent Number: 5,118,667
[45] Date of Patent: Jun. 2, 1992

[54] BONE GROWTH FACTORS AND INHIBITORS OF BONE RESORPTION FOR PROMOTING BONE FORMATION

[75] Inventors: Steven W. Adams, Sunnyvale; Rosa Armstrong, Palo Alto; David Rosen, San Jose, all of Calif.

[73] Assignee: Celtrix Pharmaceuticals, Inc., Palo Alto, Calif.

[21] Appl. No.: 695,310

[22] Filed: May 3, 1991

[51] Int. Cl.$^5$ ............... A61K 37/36; A61K 37/43
[52] U.S. Cl. ............................ 514/12; 514/21; 514/8
[58] Field of Search ...................... 514/12, 21, 8

[56] References Cited

U.S. PATENT DOCUMENTS

| | | |
|---|---|---|
| 4,294,753 | 10/1981 | Urist . |
| 4,434,094 | 2/1984 | Seyedin et al. . |
| 4,455,256 | 6/1984 | Urist . |
| 4,608,199 | 8/1986 | Caplan et al. . |

FOREIGN PATENT DOCUMENTS

| | | |
|---|---|---|
| 0212474 | 3/1987 | European Pat. Off. . |
| 0436469 | 7/1991 | European Pat. Off. . |
| 8800205 | 1/1988 | PCT Int'l Appl. . |
| 8909787 | 10/1989 | PCT Int'l Appl. . |
| 8909788 | 10/1989 | PCT Int'l Appl. . |

OTHER PUBLICATIONS

Sawchenko et al., *Nature* (1988) 334:615-617.
Slovik et al., *J. Bone & Min. Res.* (1986) 1(4):377-381.
Totsuka et al., *Biochem. Biophys. Res. Comm.* (1988) 156:335-339.
Urist et al., *Clin. Orthop. Rel. Res.* (1982) 162:219-232.
Urist et al., *Proc. Natl. Acad. Sci.* (1984) 81:371-375.
Urist et al., *Science* (1983) 220:680-685.
Vale et al., *Nature* (1986) 321:776-779.
Vale et al., *Recent Progress in Hormone Research* (1988) 44:1-34.
Yu et al., *Nature* (1987) 330:765-767.
Bentz et al., *J. Biol. Chem.* (1989) 264:20805-20810.
Broxmeyer et al., *Proc. Natl. Acad. Sci.* (1988) 85:9052-9056.
Centrella et al., *J. Biol. Chem.* (1987) 262:2869-2874.
Cheifetz et al., *J. Biol. Chem.* (1988) 263:17225-17228.
Chenu et al., *Proc. Natl. Acad. Sci.* (1988) 85:5683-5687.
Isgaard et al., *Endocrinol. Metab.* (1986) 13:E367-E372.
Joyce et al., *J. Cell. Biol.* (1990) 110:2195-2207.
Murata et al., *Proc. Natl. Acad. Sci.* (1988) 85:2334-2438.
Noda et al., *Endocrinology* (1989) 124(6):2991-2994.
Kiebzak et al., *J. Bone Min. Res.* (1988) 3:439-446.
Ozkaynak et al., *EMBO J.* (1980) 9:2085-2093.
Pfeilschifter et al., *Proc. Natl. Acad. Sci.* (1987) 84:2024-2028.
Sampath et al., *J. Biol. Chem.* (1990) 265:13198-13205.
Wozney, *Progress in Growth Factor Research* (1989) 1:267-280.

*Primary Examiner*—Howard E. Schain
*Assistant Examiner*—Choon Koh
*Attorney, Agent, or Firm*—Morrison & Foerster

[57] ABSTRACT

Bone growth factors are used to stimulate new bone formation when administered with agents that inhibit bone resorption. These therapeutic combinations result in an enhanced rate of bone formation with an increase in bone mass.

68 Claims, 4 Drawing Sheets

BONE GROWTH FACTORS AND INHIBITORS OF BONE RESORPTION FOR PROMOTING BONE FORMATION

FIELD OF THE INVENTION

The instant invention relates generally to polypeptide factors and their use in bone growth and maturation. Specifically, the invention relates to the use of bone growth factors to stimulate new bone formation when used with agents that inhibit bone resorption. These therapeutic combinations result in an enhanced rate of bone formation with an increase in bone mass.

BACKGROUND OF THE INVENTION

The transforming growth factor beta (TGF-$\beta$) family has been implicated in a variety of physiological processes involving bone in vivo and in vitro. For example, in in vitro studies, TGF-$\beta$ stimulates proliferation and matrix synthesis of osteoblastic cells (Centrella, et al. (1987) *J. Biol. Chem.* 262:2869-2874) and has been reported to inhibit the formation and activity of osteoclastic cells (Chenu, et al. (1988) *Proc. Natl. Acad. Sci. U.S.A.* 85:683-5687; Kiebzak, et al. (1988) *J. Bone Min. Res.* 3:439-446). In vivo, subperiosteal injections of TGF-$\beta$ in the femur (Joyce, et al. (1990) *J. Cell. Biol.* 110:2195-2207) and calvarium (Noda and Camilliere (1989) *Endocrinology* 124:2991-2294) of rodents stimulate local bone formation. Furthermore, mice injected daily subcutaneously with TGF-$\beta$ showed an increase in the number of cuboidal osteoblasts along with increased deposition of bone matrix, while rats similarly treated showed an increase in osteoblasts, demonstrating the systemic in vivo activity of TGF-$\beta$ on bone (Matthews, et al. "Systemic delivery of TGF-$\beta$ produces a marked increase in osteoblasts, stimulates osteoid synthesis and increases bone formation in long bones and vertebrae in rats and mice," poster presented at the 1990 Meeting of the American Society of Bone and Mineral Research).

Activins are dimeric proteins structurally similar to inhibin, TGF-$\beta$1, TGF-$\beta$2, and other proteins that makeup a family of proteins structurally related to TGF-$\beta$1. These proteins exhibit the chromatographic properties of TGF-$\beta$s. In addition to having homology with respect to the amino acid sequences, activins exhibit conservation of cysteine positions characteristic of the TGF-$\beta$s. Activins exhibit a molecular weight of 25 kD under nonreducing conditions by SDS-PAGE (and a molecular weight of 14 kD under reducing conditions). There are two known forms of the activin subunits, which have been termed $\beta$A or $\beta$B. Homodimeric forms $\beta$AA and $\beta$BB and a heterodimeric form $\beta$AB have been described in the literature. Activin subunits have about a 30% homology to TGF-$\beta$1 and TGF-$\beta$2 chains in terms of their amino acid sequences. Inhibins are polypeptides which are also structurally related to activins. Inhibins are heterodimers of the activin $\beta$A or $\beta$B subunit and a separate $\alpha$ subunit. Inhibins exhibit activity essentially opposite to activin.

The activin $\beta$A homodimer and $\beta$AB heterodimer have been purified from porcine follicular fluid, and have been shown to stimulate the release of follicle stimulating hormone (FSH) from rat pituitary cells in vitro (W. Vale et al., *Nature* (1986) 321:776-79). Other reported activities include stimulation of oxytocin release from neurosecretory neurons (P. E. Sawchemko, et al., *Nature* (1988) 334:615-17; W. Vale et al., "Recent Progress in Hormone Research" (1988) 44:1-34); stimulation of insulin secretion from pancreatic islets (Y. Totsuka et al., *Biochem. & Biophys. Res. Comm.* (1988) 156:335-39); and stimulation of erythroid and multipotential progenitor cell colony formation in bone marrow culture (J. Yu et al., *Nature* (1987) 330:765-67; H. E. Broxmeyer et al., *Proc. Natl. Acad. Sci. U.S.A.* (1988) 85:9052-56). Activin $\beta$A is apparently identical to erythroid differentiation factor (EDF) (M. Murata et al., *Proc. Natl. Acad. Sci. U.S.A.* (1988) 85:2434-38).

Despite the fact that activin is similar in amino acid sequence to TGF-$\beta$, activin does not compete with TGF-$\beta$ for binding to TGF-$\beta$ receptors types I, II, or III present on fibroblasts and epithelial cells. However, activin has been reported to compete against binding of TGF-$\beta$1 to rat pituitary tumor cells (S. Cheifetz et al., *J. Biol. Chem.* (1988) 263:17225-28). TGF-$\beta$1 and TGF-$\beta$2 have been reported to induce formation of endochondral bone in vivo (M. E. Joyce et al., *J. Cell Biol.* (1990) 110:2195-2207, H. Bentz, et al. (1989) *J. Biol. Chem.*, 264:20805-10).

A "bone morphogenetic protein" (BMP) was extracted from demineralized bone using urea or guanidine hydrochloride and reprecipitated according to the disclosures in U.S. Pat. Nos. 4,294,753 and 4,455,256 to Urist. Urist subsequently reported (Urist. M. R., *Clin. Orthop. Rel. Res.* (1982) 162:219) that ion exchange purification of this crude protein mixture yielded an activity which was unadsorbed to carboxymethyl cellulose resin (CMC) at pH 4.8. Urist's reports in *Science* (1983) 220:680-685 and *Proc. Natl. Acad. Sci. U.S.A.* (1984) 81:371-375 describe BMPs having molecular weights of 17,500 and 18,500 daltons. Urist's patent publication, EPA Publication No. 0212474, describes BMP fragments of 4,000 to 7,000 daltons obtained by limited proteolysis of BMP.

U.S. Pat. No. 4,608,199 describes a bone-derived protein of 30,000-32,000 daltons. The protein is described as being water soluble and having no affinity for concanavalin A.

WO 88/00205 reports four proteins, designated BMP-1, BMP-2 Class I ("BMP-2"), BMP-3, and BMP-2 Class II ("BMP-4"), that are alleged to have osteogenic activity.

J. M. Wozney, in *Growth Factor Research*, Vol. 1 (1989), pp. 267-280, describes three additional BMP proteins closely related to BMP-2, and which have been designated BMP-5, BMP-6 and BMP-7.

WO 89/09787 and 89/09788 describe a protein called "OP-1", now known to be BMP-7. The cloning of BMP-7 is described in E. Ozkaynak et al., *EMBO Journal* (1990) 9:2085-2093, and the purification of BMP-7 is described in T. K. Sampath et al., *J. Biol. Chem.* (1990) 265:13198-13205.

U.S. Pat. No. 4,434,094 to Seyedin and Thomas reported the partial purification of a bone generation-stimulating, bone-derived protein by extraction with chaotropic agents, fractionation on anion and cation exchange columns, and recovery of the activity from a fraction adsorbed to CMC at pH 4.8. This new protein fraction was termed "osteogenic factor" and was characterized as having a molecular weight below about 30,000 daltons.

Isgaard, et al. (*Endocrinol. Metab.* 13:E367-72,1986) reports the stimulation of bone growth by insulin-like growth factor (IGF).

Slovik et al. (*J. Bone & Min. Res.* 1:377-381, 1986) report the stimulation of bone growth by parathyroid hormone (PTH).

In vitro evidence suggests resorption of bone and formation of new bone appear to be coupled in some fashion. TGF-$\beta$, for example, is apparently involved in this process. Pfeilschifter and Mundy, *Proc. Natl. Acad. Sci. U.S.A.* (1987) 84:2024-2028), demonstrated that calvariae incubated with parathyroid hormone, 1,25-dihydroxyvitamin $D_3$, and interleukin 1, all factors that stimulate bone resorption, showed an increase in endogenous TGF-$\beta$ activity in the culture medium, whereas incubation with calcitonin, which inhibits bone resorption, correlated with a decrease in endogenous TGF-$\beta$ activity.

The present invention offers in vivo combination therapy for stimulating new bone formation through the combined administration of an exogenous bone growth factor and an agent which inhibits bone resorption. These combinations provide more effective therapy for prevention of bone loss and replacement of bone than the components alone, as the combination appears to synergistically enhance the increase in bone mass and the rate of bone formation.

SUMMARY OF THE INVENTION

The present invention includes a method for stimulating new bone formation in a subject by administration of the combination of a bone growth factor and an inhibitor of bone resorption. Preferably, the bone growth factor is TGF-$\beta$, activin, BMP, IGF, PTH, or active fragments thereof, and the inhibitor of bone resorption is an estrogen, bisphosphonate, sodium fluoride, calcitonin, or tamoxifen, or related compounds.

Another aspect of the invention is a method for treating bone loss in a subject by administration of the combination of a bone growth factor and an inhibitor of bone resorption.

The invention further provides for a composition of a bone growth factor and an inhibitor of bone resorption for inducing bone formation in a subject.

Another aspect of the invention is a composition of a bone growth factor and an inhibitor of bone resorption for treatment of bone loss in a subject.

DETAILED DESCRIPTION OF THE INVENTION

A. Definitions

It must be noted that as used in this specification and the appended claims, the singular forms "a", "an" and "the" include plural referents unless the context clearly dictates otherwise. Thus, for example, reference to "a TGF-$\beta$" includes statistical mixtures of dimeric proteins of the type generally described herein; and reference to "the method of administration" includes one or more methods of the type described herein and/or of the type which will become apparent to those of ordinary skill in the art upon reading this disclosure.

The term "bone growth factor" refers to the families of proteins which affect bone or cartilage formation. Examples of bone growth factors include transforming growth factor-beta (TGF-$\beta$), activin, IGF, PTH, and bone morphogenic factor (BMP).

The term "TGF-$\beta$" refers to beta-type transforming growth factors, including TGF-$\beta$1, TGF-$\beta$2, TGF-$\beta$3, TGF-$\beta$4, TGF-$\beta$5, heterodimers of the TGF-$\beta$ polypeptide chains (e.g. TGF-$\beta$1.2), and fragments thereof, synthetic peptides, and homologous proteins having substantially equivalent biological activity in any of the numerous known TGF-$\beta$ assays, such as the one described in *Methods for Preparation of Media, Supplements, and Substrate for Serum-free Animal Cell Culture* (1984) pp. 181-194. Alan R. Liss, Inc. This particular assay determines ability to induce anchorage-dependent growth in non-neoplastic normal rat kidney (NRK) fibroblasts by measuring the formation of cell colonies in soft agar. Other known TGF-$\beta$ activity assays include but are not limited to stimulation of osteoblast proliferation, inhibition of keratinocyte proliferation, stimulation of collagen synthesis in a variety of cells, inhibition of mitogen-stimulated T-cell proliferation, and stimulation of chemotactic activity. Preparation of TGF-$\beta$1 and TGF-$\beta$2 is described in U.S. Pat. No. 4,774,322, incorporated herein by reference. Additional TGF-$\beta$s have also been described. U.S. Pat. No. 4,886,747 describes the identification of TGF-$\beta$3 and its nucleotide sequence, and describes a method for recovery of TGF-$\beta$ from recombinant cell cultures. S. B. Jakowlew et al., *Molec. Endocrinol.* (1988) 2:1186-1195, describes TGF-$\beta$4 and its nucleotide sequence, identified by cDNA characterization. A. B. Roberts et al., *Growth Factors*, Vol. 2 (1990) pp. 135-147, describes the purification of TGF-$\beta$5 from Xenopus-conditioned medium.

The term "TGF-$\beta$" as used herein is also intended to include the heterodimer TGF-$\beta$2.3, disclosed in co-pending patent application U.S. Ser. No. 614,306, filed Nov. 16, 1990. TGF-$\beta$2.3 may be prepared from an extract of bone by pooling side fractions from peaks of column chromatography, subjecting those fractions to reverse phase HPLC and recovering those fraction which migrate more slowly than TGF-$\beta$2 by SDS-PAGE, subjecting those slower migrating fractions to FPLC and recovering those that migrate during a pH 4.6 to 6.7 gradient, subjecting the pH 4.6 to 6.7 eluant to reverse phase HPLC or gel electrophoresis, and recovering substantially pure TGF$\beta$2.3.

The term "TGF-$\beta$" as used herein is also intended to include any other synthetic molecule whose mechanism of action is mediated through the TGF-$\beta$ receptor or second messsenger pathway.

Because these proteins are non-species-specific in their activity they maybe used to treat subjects in general, including sport, pet, and farm animals, and humans.

The term "inhibition of bone resorption" refers to prevention of bone loss, especially the inhibition of removal of existing bone either from the mineral phase and/or the organic matrix phase, through direct or indirect alteration of osteoclast formation or metabolism. Thus, the term "inhibitor of bone resorption" as used herein refers to agents that prevent bone loss by the direct or indirect alteration of osteoclast formation or metabolism.

The term "osteogenically effective" means that amount which effects the formation and differentiation of mature bone. As used herein, an osteogenically effective dose is also "pharmaceutically effective."

The term "subject" as used herein refers to a living vertebrate animal such as a mammal or bird in need of treatment, i.e., in need of bone repair or replacement. Such need arises locally in cases of bone fracture, nonunion, defect, prosthesis implantation, and the like. Such need also arises in cases of systemic bone disease, as in osteoporosis, osteoarthritis, Paget's disease, osteomalacia, osteohalisteresis, multiple meyeloma and other forms of cancer, and age-related loss of bone mass.

The term "treatment" as used herein shall mean (1) providing a subject with an amount of a substance sufficient to act prophylactically to prevent the development of a weakened and/or unhealthy state; or (2) providing a subject with a sufficient amount of a substance so as to alleviate or eliminate a disease state and/or the symptoms of a disease state, and a weakened and/or unhealthy state.

B. General methods

Drugs which prevent bone loss and/or add back lost bone may be evaluated in the ovariectomized rat. This animal model is well established in the art (see, for example, Wronski, et al. (1985) *Calcif. Tissue Int.* 37:324-328; Kimmel, et al. (1990) *Calcif. Tissue Int.* 46:101-110; and Durbridge, et al. (1990) *Calcif. Tissue Int.* 47:383-387; these references are hereby incorporated in their entirety). Wronski, et al. ((1985) *Calcif. Tissue Int.* 43:179-183)) describe the association of bone loss and bone turnover in the ovariectomized rat.

Examples of inhibitors of bone resorption include estrogens, bisphosphonates, calcitonins, sodium fluorides, and tamoxifens (Turner, et al. (1987) *J. Bone Mineral Res.* 2:115-122; Wronski, et al. (1988) *Endocrinology* 128:681-686; and Wronski, et al. (1989) *Endocrinology* 125:810-816; Pfeilshifter, et al. (1987) *Proc. Natl. Acad. Sci. U.S.A.* 84:2024-2028; Turner, et al. (1988) *Endocrinology* 122:1146-1150). The entire molecule of a particular inhibitor may be used, or alternatively, only a functional part of the inhibitor molecule may be used.

Pharmaceutical formulations of the invention which include a bone growth factor and/or an inhibitor of bone resorption for administration will generally include an osteogenically effective amount of the bone growth factor to promote bone growth, in addition to a pharmaceutically acceptable excipient. Suitable excipients include most carriers approved for parenteral administration, including water, saline, Ringer's solution, Hank's solution, and solutions of glucose, lactose, dextrose, ethanol, glycerol, albumin, and the like. These compositions may optionally include stabilizers, antioxidants, antimicrobials, preservatives, buffering agents, surfactants, and other accessory additives. The TGF-$\beta$ and inhibitor of bone resorption may also be delivered in a slow release form from a suitable carrier.

A presently preferred vehicle comprises about 1 mg/ml serum albumin (species-specific) in phosphate-buffered saline (PBS) or isotonic citrate buffer. A thorough discussion of suitable vehicles for parenteral administration may be found in E. W. Martin, "Remington's Pharmaceutical Sciences" (Mack Pub. Co., current edition sections relating to the excipient vehicles and formulating being incorporated herein by reference to disclose such). Such formulations are generally known to those skilled in the art and are administered systemically to provide systemic treatment.

A bone growth factor and an agent which inhibits bone resorption may be administered sequentially or simultaneously as a single composition to the subject. If administered sequentially, the period between the administration of the bone growth factor and the inhibitor of bone resorption will typically be one week to one year, and optimally, one week to six months.

If the bone growth factor and the agent which inhibits bone resorption are administered as a single composition, the molar ratio of bone growth factor to inhibitor of bone resorption will be about 10:1 to 1:10, preferably, 5:1 to 1:5, and optimally, 1:1. The optimal ratio is expected to vary from compound to compound. Furthermore, if administered as a single composition, the bone growth factor and the inhibitor of bone resorption may be separate components of the composition, or they may be conjugated to each other. Methods for conjugating bone growth factors to other agents are described above.

The precise dosage necessary will vary with the age, size, sex and condition of the subject, the nature and severity of the disorder to be treated, and the like; thus, a precise effective amount cannot be specified in advance and will be determined by the caregiver. However, appropriate amounts may be determined by routine experimentation with animal models, as described below. In general terms, an effective dose of a bone growth factor for systemic treatment will range from about 0.001 $\mu$g/kg to about 10 mg/kg of body weight. An effective dose for estrogen is about 1 $\mu$g/kg to about 1 mg/kg of body weight. An effective dose for bisphosphonates is about 0.05 $\mu$g/kg to about 15 mg/kg of body weight. An effective dose for calcitonin is about 0.05 MRCU (Medical Research Council Units)/kg to about 2.5 MRCU/kg of body weight.

Effective doses for local administration would be about 0.001 $\mu$g to 1 mg per application site.

The methods and compositions of the invention are useful for treating bone fractures, defects, and disorders which result in weakened bones such as osteoporosis, osteoarthritis, Paget's disease, osteohalisteresis, osteomalacia, bone loss resulting from multiple myeloma and other forms of cancer, bone loss resulting from side effects of other medical treatment (such as steroids), and age-related loss of bone mass.

In accordance with one method of use, the bone growth factor and the inhibitor of bone resorption may be administered systemically either orally and/or parenterally, including subcutaneous or intravenous injection, and/or intranasally. Additionally, the bone growth factor and the inhibitor of bone resorption make be delivered in a slow release form from a suitable carrier.

In accordance with another method of use, the bone growth factor may be administered locally to a specific area in need of bone growth or repair, with either the concomitant administration of the inhibitor of bone resorption at the site, or the administration of the inhibitor of bone resorption in a separate vehicle, or, the inhibitor of bone resorption may be provided locally, with the administration of the bone growth factor in a separate vehicle. Thus, the bone growth factor and/or inhibitor of bone resorption may be implanted directly at the site to be treated, for example, by injection or surgical implantation in a sustained-release carrier. Suitable carriers include hydrogels, controlled- or sustained-release devices (e.g., an Alzet® minipump), polylactic acid, and collagen matrices. Presently preferred carriers are formulations of atelopeptide collagen containing particulate calcium phosphate mineral components, such as combinations of homologous or xenographic fibrillar atelopeptide collagen (for example Zyderm® Collagen Implant, available from Collagen Corporation, Palo Alto, Calif.) with hydroxyapatitetricalcium phosphate (HA-TCP, available from Zimmer, Inc., Warsaw, In.). It is presently preferred to administer implant compositions containing a bone growth factor and/or an inhibitor of bone resorption in a collagen/mineral mixture implant.

Bone growth factors and/or an inhibitor of bone resorption, delivered in sustained-release vehicles is also particularly useful for improving implant fixation, for example for improving ingrowth of new bone into a metal prosthesis in joint reconstruction and dental or orthopedic implants. Alternatively, the bone growth factor may be delivered in the implant, with the inhibitor delivered in a separate vehicle, and vice-versa.

Dental and orthopedic implants can be coated with bone growth factors in combination with an inhibitor of bone resorption, to enhance attachment of the implant device to the bone. Alternatively, the bone growth factor can be used to coat the implant, and the inhibitor of bone resorption can be administered concomitantly or sequentially in a separate vehicle, and vice-versa.

In general, implant devices may be coated with a bone growth factor and/or an inhibitor of bone resorption as follows. The bone growth factor (and the inhibitor of bone resorption, if desired) is dissolved at a concentration in the range of 0.01 μg/ml to 200 mg/ml in phosphate-buffered saline (PBS) containing 2 mg/ml serum albumin. The porous end of an implant is dipped in the solution and is airdried (or lyophilized) or implanted immediately into the bony site. The viscosity of the coating solution is increased, if desired, by adding hyaluronate at a final concentration of 0.1 mg/ml to 100 mg/ml or by adding other pharmaceutically acceptable excipients. Alternatively, the solution containing the bone growth factor (and the inhibitor of bone resorption, if desired) is mixed with collagen gel or human collagen (e.g. Zyderm® Collagen Implant, Collagen Corp., Palo Alto, Calif.) to a final collagen concentration of 2 mg/ml to 100 mg/ml to form a paste or gel, which is then used to coat the porous end of the implant device. The coated implant device is placed into the bony site immediately or is airdried and rehydrated with PBS prior to implanting, with the objective of maximizing new bone formation into the implant while minimizing the ingrowth of soft tissue into the implant site.

C. EXAMPLES

The following examples are put forth so as to provide those of ordinary skill in the art with a complete disclosure and description of how to extract, isolate, formulate and use the compositions and methods of the invention and are not intended to limit the scope of what the inventors regard as their invention. Efforts have been made to insure accuracy with respect to numbers used (e.g., amounts, times, temperature, etc.), but some experimental error and deviations should be accounted for. Unless indicated otherwise, parts are parts by weight, temperature is in degrees centigrade, pressure is at or near atmospheric, and other parameters are conventional and in accordance with those normally accepted by those skilled in the art.

EXAMPLE 1

Twenty-five day old Sprague-Dawley rats were either ovariectomized (OVX) or sham operated and housed to allow bone loss for eight weeks. Five ovariectomized and three sham operated rats received 5 μg TGF-$\beta$2 subcutaneously daily for 7 days. Four ovariectomized rats received vehicle only daily for 7 days. Rats were euthanized at the end of 7 days treatment and femurs were dissected from soft tissue.

Bone specimens were fixed in ethanol, processed and embedded undecalcified in methylmethacrylate. Thin sections (4 μm) of the distal femur were cut on a Reichert-Jung microtome. Thin sections were stained with toluidine blue for general morphology.

Qualitative evaluation was performed on femurs from rats in the above groups. Both trabecular bone and cortical endosteal surfaces in the sham controls were generally quiescent (i.e. little osteoblastic or osteoclastic activity). By contrast, in the sham plus TGF-$\beta$ treatment group, osteoblasts and osteoclasts were more easily recognized than either the sham controls or either OVX group.

Thus, these observations provide evidence of increased bone turnover in sham operated animals when treated with TGF-$\beta$ compared with non-treated sham operated rats. Since the same extent of bone turnover was not seen in ovariectomized rats treated with TGF-$\beta$ compared with vehicle-treated ovariectomized controls, it appears that intact animals possess a factor(s) that is absent in the ovariectomized animal.

EXAMPLE 2

Forty two Sprague-Dawley rats, 90 days old, were ovariectomized and housed to allow bone loss for 10 weeks after surgery. At 70 days post-surgery, rats were treated daily with TGF-$\beta$2 at 5 μg/animal with or without 17$\beta$-estradiol at 10 μg/kg (5 days/week) for 2 weeks. Additional groups of ovariectomized rats were treated with vehicle alone or 17$\beta$-estradiol alone as a control. Each group consisted of 6 rats.

Bone was metabolically labeled with fluorochrome markers, calcein, and tetracycline. Calcein was given 7 days before euthanasia and tetracycline 2 days before euthanasia to allow evaluation of rate of mineralization and bone formation.

The first lumbar vertebra and tibias were cleaned of all adhering soft issue and defatted in acetone for 2 days at room temperature. After drying for 1 hour, bones were further dried for 2 days in an oven at 80° C., cooled for one hour, and weighed on an analytical balance. The bones were then ashed in a muffle furnace for 2 hours at 600° C. and cooled for 45 minutes in a desiccator. The bone samples were charred on a hot plate during addition of 2NHNO3, and final charring done over an open flame. The samples were then ashed for 24 hours in a muffle furnace at 600° C., cooled for 45 minutes in a desiccator, and weighed again to obtain the ash/dry weight of bone.

Bone specimens for histology were dehydrated in ethanol and embedded undecalcified in methylmethacrylate. Thin sections (4 μm) and thick sections (15 μm of the distal femur were cut on a Reichert-Jung 2050 microtome. Thin sections were stained with toluidine blue to evaluate general morphology and deposition of osteoid. Thick sections were left unstained to assess the dynamic parameters of bone turnover indicated by the fluorochrome markers.

Measurements of dry weights and ash weights were used to calculate a ratio of organic to inorganic content of both the tibia and the first lumbar vertebra. The results are shown in FIGS. 3 and 4.

Figure 3:
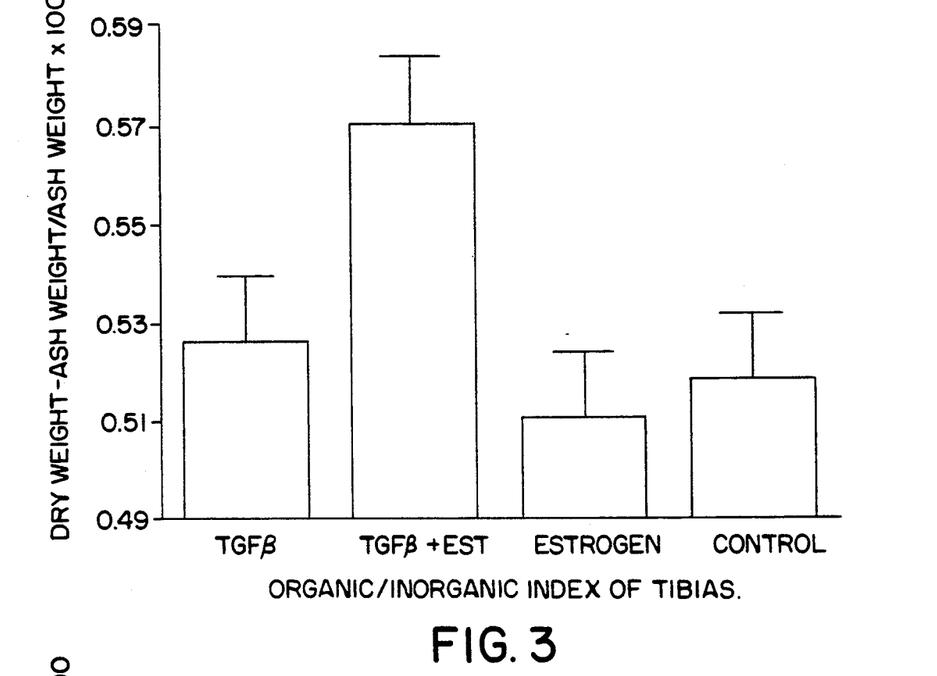
FIG. 3 is a graph comparing the ratio of organic to inorganic content of bone from ovariectomized rats and ovariectomized rats treated with estrogen.

As demonstrated in FIG. 3, treatment with estrogen alone resulted in a slight decrease in the organic/inorganic ratio of tibias when compared to non-treated OVX controls, and TGF-$\beta$2 at 5 μg/animal resulted in a small increase in the organic/inorganic ratio. However, when TGF-$\beta$2 was administered with 17$\beta$-estradiol the organic/inorganic ratio was far greater than with either agent alone, and was significantly greater than the non-treated OVX control.

Figure 4:
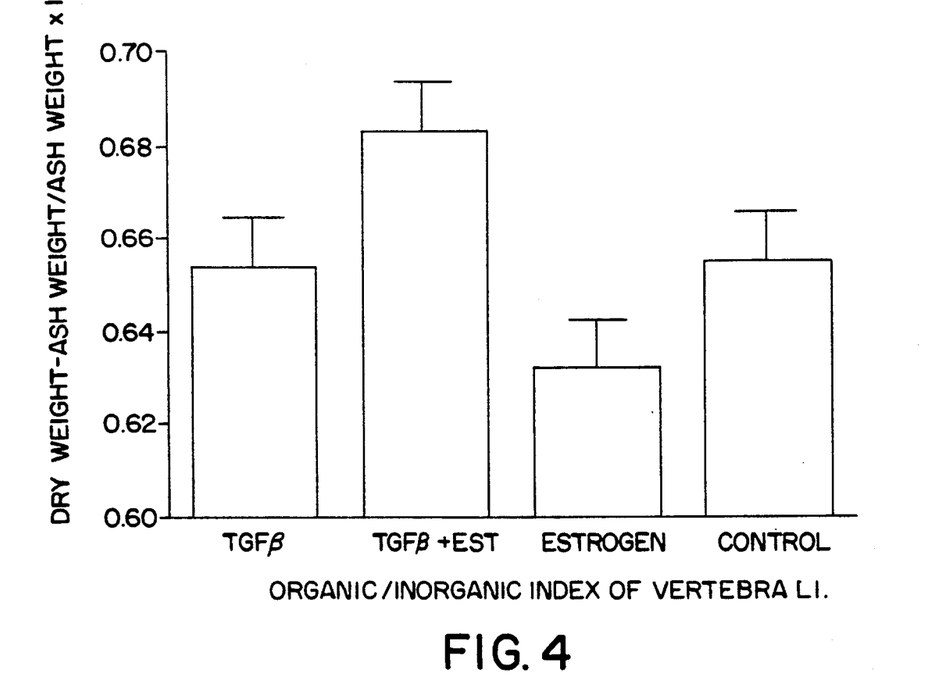
FIG. 4 is a graph comparing the ratio of organic to inorganic content of bone from ovariectomized rats and ovariectomized rats treated with TGF-$\beta$ and TGF-$\beta$ plus estrogen.

A similar result was seen when evaluating the vertebrae L1 as shown in FIG. 4. A decrease in the organic/inorganic ratio was seen with estrogen alone. In this site, no increase in organic/inorganic ratio was seen with treatment with TGF-$\beta$ alone, although treatment with TGF-$\beta$ plus 17-$\beta$estradiol resulted in a significant increase in the organic/inorganic ratio when compared with non-treated OVX controls.

Examination of stained sections indicated that non-treated OVX control animals and rats treated with estrogen had very small amounts of osteoid deposition on trabecular surfaces. In contrast, rats treated with TGF-$\beta$ had significant increases in the total amount of stainable osteoid. Rats that had received both TGF-$\beta$ and estrogen had even larger amounts of osteoid deposition than with either factor alone.

Figure 1A:
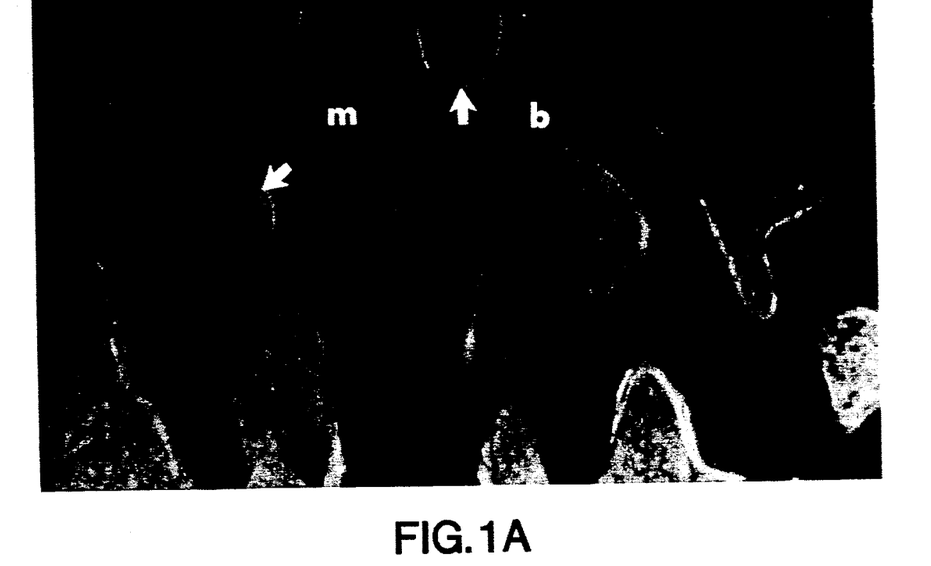
FIGS. 1A and 1B are photomicrographs depicting the double fluorochrome labeling of trabecular surfaces in ovariectomized rats (A) and ovariectomized rats treated with estrogen (B).
Figure 1B:
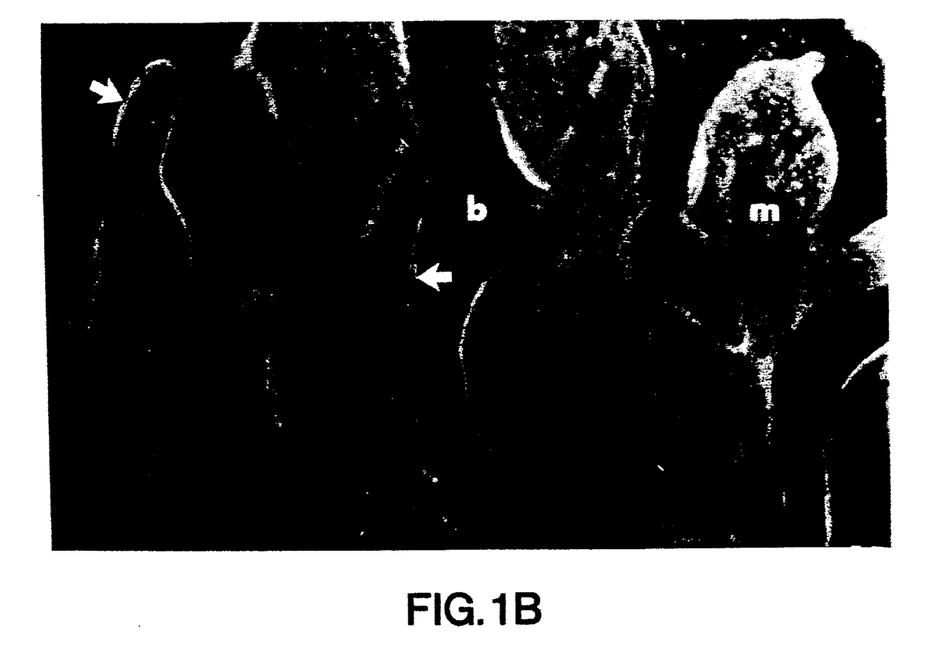
Figure 2A:
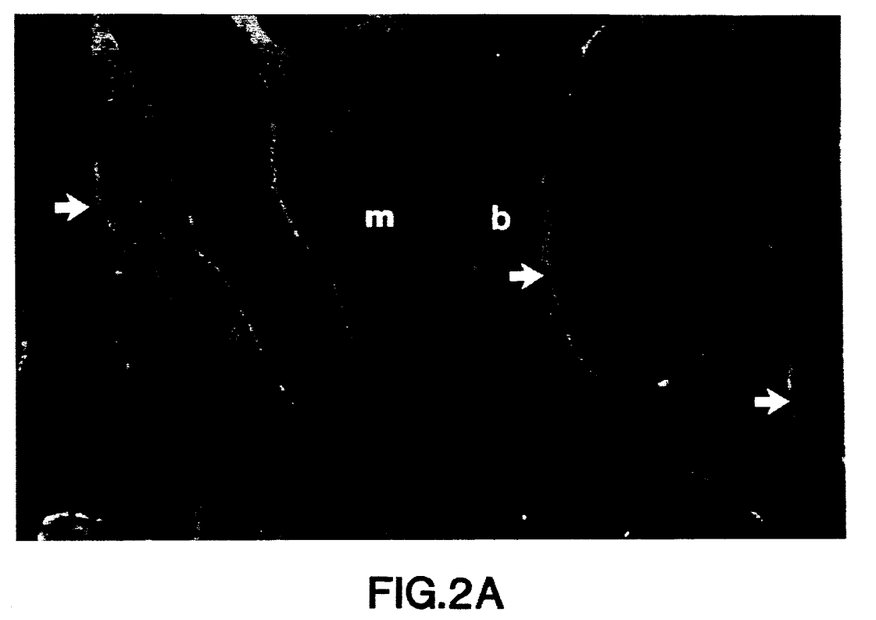
FIGS. 2A and B are photomicrographs depicting the double fluorochrome labeling of trabecular surfaces in ovariectomized rats receiving TGF-$\beta$ (A) or TGF-$\beta$ and estrogen (B).
Figure 2B:
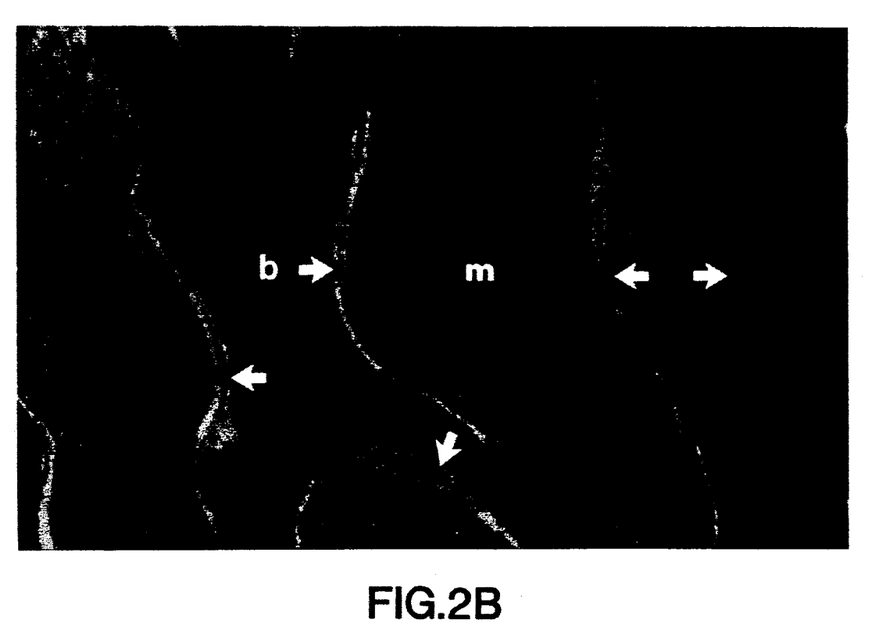

Qualitative examination of unstained sections indicated that non-treated OVX rats and rats treated with estrogen had small amounts of trabecular surface containing double fluorochrome labels (FIGS. 1A and 1B; 15 μm sections viewed with a fluorescence microscope at a magnification of 40X; b denotes bone; m denotes bone marrow; double-labeled surface are indicated by arrows). Rats treated with TGF-$\beta$ had increased amounts of double-labeled trabecular surface, compared to the previous two groups, while those that had received TGF-$\beta$ and estrogen showed the highest levels of double labelled surfaces of all experimental groups. This correlated well with the increases in deposition of osteoid and the wider osteoid seams described above.

The histomorphometric data were collected in the epiphyseal spongiosa of femurs. One row of fields was measured at 250X from cortex to cortex, and usually 10-14 fields were measured in each section. The corticoendosteal surfaces were not included in the measurements. Total perimeter (surface) and area (volume) of trabecular bone (Perimeter (mm) /Area (mm$^2$)=bone volume) were traced onto a graphics table and interfaced with a Mackintosh computer. The percent of total trabecular surface covered by a single label (sLS) or a double label (dLS) was traced to calculate the per cent mineralizing surface (MS) by the formula, $$\% \ MS = \frac{(dLS - sLS/2)}{BS}$$

where BS denotes bone surface. Mineral appositional rates (MAR) were obtained by dividing the interlabel width by the interlabel time in days and correcting for the section obliquity to yield the corrected MAR in μm/day (Multiplied by 0.365 to correct to μg/yr). Bone formation rates (BFR) were computed conservatively using dLS only as follows:

$$dLS \times corr.MAR/BV = BFR.$$

Figure 5A:
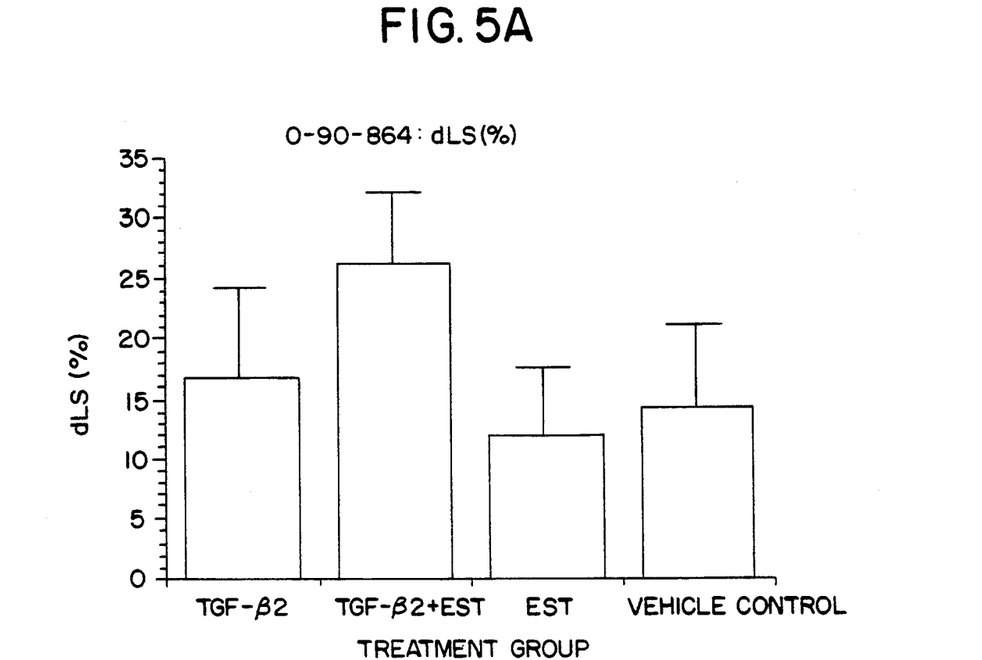
FIGS. 5A/B is a graph comparing the percent of double-labelled bone surface in ovariectomized rats treated with TGF-$\beta$, estrogen, TGF-$\beta$+estrogen, or vehicle alone.
Figure 5B:
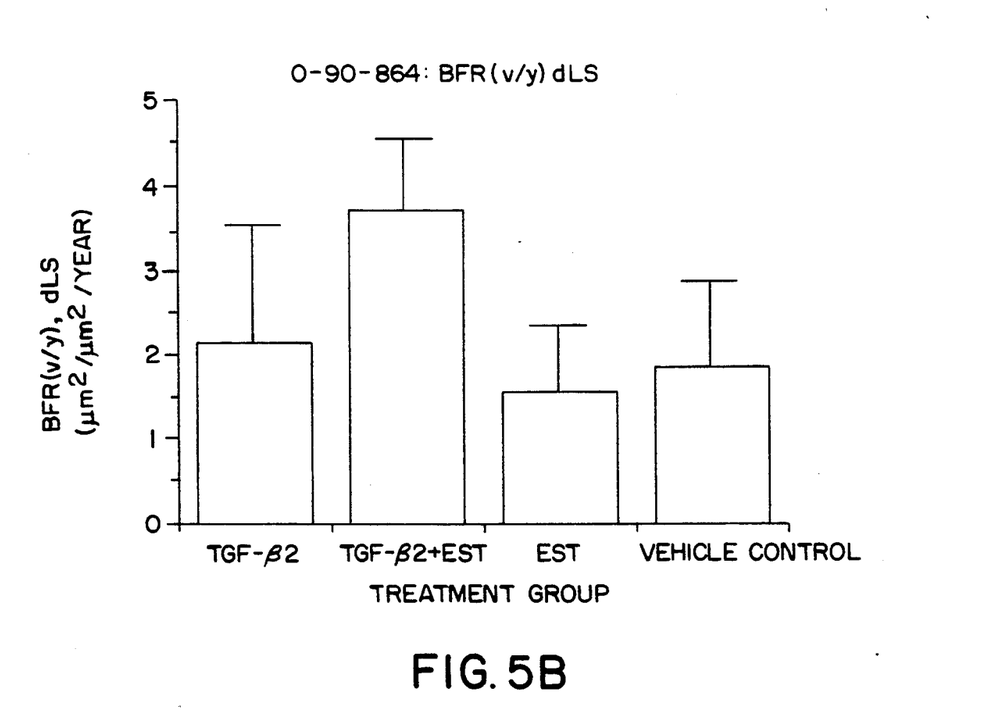
FIG. 5B is a graph comparing the rate of bone formation in ovariectomized rats treated with TGF-$\beta$, estrogen, TGF-$\beta$+estrogen, or vehicle alone.

Data were expressed as a mean±SE, and comparisons among groups were made using one factor ANOVAS. These data are shown in FIGS. 5A and 5B, where FIG. 5A depicts the synergistic effect of TGF-$\beta$ and estrogen in ovariectomized rats, and FIG. 5B depicts the synergistic rate of bone formation in ovariectomized rats treated with TGF-$\beta$ and estrogen.

Thus, the treatment of the ovariectomized rat with TGF-$\beta$ resulted in increased bone formation. This increase, however, was significantly enhanced by concomitant treatment with estrogen.

We claim:

1. A method for stimulating new bone formation in a subject, comprising administering a pharmaceutically effective dose of a bone growth factor and a pharmaceutically effective dose of an inhibitor of bone resorption to the subject.
2. The method of claim 1, wherein the bone growth facto is TGF-$\beta$.
3. The method of claim 1, wherein the bone growth factor is an activin.
4. The method of claim 1, wherein the bone growth factor is a bone morphogenic protein (BMP).
5. The method of claim 1, wherein the bone growth factor is an IGF.
6. The method of claim 1, wherein the bone growth factor is parathyroid hormone (PTH).
7. The method of claim 1, wherein the inhibitor of bone resorption is an estrogen.
8. The method of claim 1, wherein the inhibitor of bone resorption is a calcitonin.
9. The method of claim 1, wherein the inhibitor of bone resorption is a bisphosphonate.
10. The method of claim 1, wherein the inhibitor of bone resorption is sodium fluoride.
11. The method of claim 1, wherein the inhibitor of bone resorption is a tamoxifen.
12. The method of claim 1, wherein the subject is human.
13. The method of claim 1, wherein the bone growth factor and the inhibitor of bone resorption are administered sequentially.
14. The method of claim 1, wherein the bone growth factor and the inhibitor of bone resorption are administered simultaneously.
15. A method for treating bone loss in a subject, comprising administering a pharmaceutically effective dose of a bone growth factor and a pharmaceutically effective dose of an inhibitor of bone resorption to the subject.
16. The method of claim 15, wherein the bone growth factor is TGF-$\beta$.

17. The method of claim 15, wherein the bone growth factor is an activin.

18. The method of claim 15, wherein the bone growth factor is a bone morphogenic protein (BMP).

19. The method of claim 15, wherein the bone growth factor is an IGF.

20. The method of claim 15, wherein the bone growth factor is parathyroid hormone (PTH).

21. The method of claim 15, wherein the inhibitor of bone resorption is an estrogen.

22. The method of claim 15, wherein the inhibitor of bone resorption is a calcitonin.

23. The method of claim 15, wherein the inhibitor of bone resorption is a bisphosphonate.

24. The method of claim 15, wherein the inhibitor of bone resorption is sodium fluoride.

25. The method of claim 15, wherein the inhibitor of bone resorption is a tamoxifen.

26. The method of claim 15, wherein the subject is human.

27. The method of claim 15, wherein the bone loss is osteoporosis-related.

28. The method of claim 15, wherein the bone loss is osteomalacia-related.

29. The method of claim 15, wherein the bone loss is osteohalisteresis-related.

30. The method of claim 15, wherein the bone loss is age-related.

31. The method of claim 15, wherein the bone loss is related to steroid therapy.

32. The method of claim 15, wherein the bone loss is osteoarthritis-related.

33. The method of claim 15, wherein the bone loss is related to Paget's disease.

34. The method of claim 15, wherein the bone loss is related to cancer.

35. The method of claim 34, wherein the cancer is multiple myeloma.

36. The method of claim 15, wherein the treatment is prophylactic.

37. The method of claim 15, wherein the bone growth factor and the inhibitor of bone resorption are administered sequentially.

38. The method of claim 15, wherein the bone growth factor and the inhibitor of bone resorption are administered simultaneously.

39. A composition for inducing bone formation in a subject, comprising a pharmaceutically effective dose of a bone growth factor and a pharmaceutically effective dose of an inhibitor of bone loss in a pharmaceutically acceptable excipient.

40. The composition of claim 39, wherein the bone growth factor is TGF-$\beta$.

41. The composition of claim 39, wherein the bone growth factor is an activin.

42. The composition of claim 39, wherein the bone growth factor is a bone morphogenic protein (BMP).

43. The composition of claim 39, wherein the bone growth factor is an IGF.

44. The composition of claim 39, wherein the bone growth factor is parathyroid hormone (PTH).

45. The composition of claim 39, wherein the inhibitor of bone resorption is an estrogen.

46. The composition of claim 39, wherein the inhibitor of bone resorption is a calcitonin.

47. The composition of claim 39, wherein the inhibitor of bone resorption is a bisphosphonate.

48. The composition of claim 39, wherein the inhibitor of bone resorption is sodium fluoride.

49. The composition of claim 39, wherein the inhibitor of bone resorption is a tamoxifen.

50. The composition of claim 39, wherein the molar ratio of bone growth protein to inhibitor of bone resorption is 10:1 to 1:10.

51. The composition of claim 39, wherein the molar ratio of bone growth protein to inhibitor of bone resorption is 5:1 to 1:1.

52. The composition of claim 39, wherein the bone growth protein is conjugated to the inhibitor of bone resorption.

53. The composition of claim 39, further comprising a sustained-release vehicle.

54. A composition for treating bone loss in a subject, comprising a pharmaceutically effective dose of a bone growth factor and a pharmaceutically effective dose of an inhibitor of bone resorption in a pharmaceutically acceptable excipient.

55. The composition of claim 54, wherein the bone growth factor is TGF-$\beta$.

56. The composition of claim 54, wherein the bone growth factor is an activin.

57. The composition of claim 54, wherein the bone growth factor is a bone morphogenic protein (BMP).

58. The composition of claim 54, wherein the bone growth factor is an IGF.

59. The composition of claim 54, wherein the bone growth factor is parathyroid hormone (PTH).

60. The composition of claim 54, wherein the inhibitor of bone resorption is an estrogen.

61. The composition of claim 54, wherein the inhibitor of bone resorption is a calcitonin.

62. The composition of claim 54, wherein the inhibitor of bone resorption is a bisphosphonate.

63. The composition of claim 54, wherein the inhibitor of bone resorption is sodium fluoride.

64. The composition of claim 54, wherein the inhibitor of bone resorption is a tamoxifen.

65. The composition of claim 54, wherein the molar ratio of bone growth factor to inhibitor of bone resorption is 10:1 to 1:10.

66. The composition of claim 54, wherein the molar ratio of bone growth factor to inhibitor of bone resorption is 5:1 to 1:1.

67. The composition of claim 54, wherein the bone growth factor is conjugated to the inhibitor of bone resorption.

68. The composition of claim 54, further comprising a sustained-release vehicle.

* * * * *